US012268559B2

(12) United States Patent
Pinch et al.

(10) Patent No.: US 12,268,559 B2
(45) Date of Patent: Apr. 8, 2025

(54) SYSTEMS AND METHODS OF DISSIPATING HEAT FROM A HANDHELD MEDICAL IMAGING DEVICE

(71) Applicant: FUJIFILM SonoSite, Inc., Bothell, WA (US)

(72) Inventors: Michael Pinch, Seattle, WA (US); Carl Fabian, Beaverton, OR (US); Brent Chauvin, Snohomish, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 268 days.

(21) Appl. No.: 17/150,866

(22) Filed: Jan. 15, 2021

(65) Prior Publication Data

US 2021/0137502 A1 May 13, 2021

Related U.S. Application Data

(62) Division of application No. 15/257,811, filed on Sep. 6, 2016, now Pat. No. 10,918,361.

(60) Provisional application No. 62/217,711, filed on Sep. 11, 2015, provisional application No. 62/214,183, filed on Sep. 3, 2015.

(51) Int. Cl.
*A61B 8/00* (2006.01)

(52) U.S. Cl.
CPC ............ *A61B 8/546* (2013.01); *A61B 8/4427* (2013.01); *A61B 8/4455* (2013.01); *A61B 8/4483* (2013.01); *A61B 8/462* (2013.01); *A61B 8/467* (2013.01)

(58) Field of Classification Search
CPC ..... A61B 8/546; A61B 8/4427; A61B 8/4455; A61B 8/4483; A61B 8/462; A61B 8/467
See application file for complete search history.

(56) References Cited

U.S. PATENT DOCUMENTS

| | | | |
|---|---|---|---|
| 5,961,465 A | 10/1999 | Kelly et al. | |
| 6,542,846 B1 | 4/2003 | Miller et al. | |
| 2002/0011660 A1* | 1/2002 | Ebihara | H01L 23/3735 257/E23.106 |
| 2003/0018267 A1 | 1/2003 | Erikson et al. | |
| 2007/0296703 A1* | 12/2007 | Bestle | G06F 3/0219 345/169 |
| 2009/0005843 A1* | 1/2009 | Smyth | A61F 7/12 607/113 |
| 2009/0210190 A1* | 8/2009 | Carlson | G01K 3/005 702/130 |
| 2011/0230794 A1 | 9/2011 | Van et al. | |
| 2012/0113590 A1 | 5/2012 | Schwiebert et al. | |
| 2012/0150038 A1 | 6/2012 | Osawa | |

(Continued)

*Primary Examiner* — John D Li
(74) *Attorney, Agent, or Firm* — Womble Bond Dickinson (US) LLP (57) ABSTRACT

Systems and methods of transmitting heat out a medical imaging device are disclosed herein. In one embodiment, a medical imaging device includes a housing having electronics and a heat sink. The heat sink is positioned near a first end of the housing, a groove that is configured to receive at least a portion of an operator's hand is positioned at a second end of the housing. A heat pipe in the housing extends from the electronics toward the first end of the housing and is configured to transfer heat produced by the electronics toward the heat sink and away from the groove.

17 Claims, 10 Drawing Sheets

(56) References Cited

U.S. PATENT DOCUMENTS

| | | | |
|---|---|---|---|
| 2012/0197124 A1* | 8/2012 | Nakamura | A61B 8/56 600/443 |
| 2013/0242542 A1* | 9/2013 | Uchimi | F21V 29/50 361/695 |
| 2014/0006658 A1* | 1/2014 | Chen | G06F 13/387 710/63 |
| 2014/0058270 A1 | 2/2014 | Davidsen et al. | |
| 2014/0076513 A1* | 3/2014 | Iwama | H05K 7/20209 165/11.1 |
| 2014/0352749 A1* | 12/2014 | Strei | H10N 10/13 136/201 |
| 2015/0372356 A1* | 12/2015 | Kossakovski | H01M 10/633 136/203 |
| 2017/0007213 A1* | 1/2017 | Motoki | B06B 1/0622 |
| 2017/0020490 A1* | 1/2017 | Ryu | A61B 8/4427 |
| 2017/0043189 A1* | 2/2017 | Stoddard | G10K 11/24 |

\* cited by examiner

SYSTEMS AND METHODS OF DISSIPATING HEAT FROM A HANDHELD MEDICAL IMAGING DEVICE

CROSS-REFERENCE TO RELATED APPLICATION(S)

The present application is a divisional of U.S. patent application Ser. No. 15/257,811, filed on Sep. 6, 2016 and claims priority to U.S. Provisional Application No. 62/214,183, titled "SYSTEMS AND METHODS OF DISSIPATING HEAT FROM A HANDHELD MEDICAL IMAGING DEVICE", filed on Sep. 3, 2015, and U.S. Provisional Application No. 62/217,711, titled "SYSTEMS AND METHODS OF DISSIPATING HEAT FROM A HANDHELD MEDICAL IMAGING DEVICE", filed on Sep. 11, 2015. The foregoing applications are incorporated by reference herein in their entireties.

APPLICATIONS INCORPORATED BY REFERENCE

The present application is related to the Applicant's following applications: U.S. patent application Ser. No. 14/256,731, entitled "HAND-HELD MEDICAL IMAGING SYSTEM WITH DEDICATED POWER SOURCE DEVICES AND ASSOCIATED APPARATUSES AND METHODS"; U.S. patent application Ser. No. 14/256,744, entitled "HAND-HELD MEDICAL IMAGING SYSTEM WITH IMPROVED USER INTERFACE FOR DEPLOYING ON-SCREEN GRAPHICAL TOOLS AND ASSOCIATED APPARATUSES AND METHODS"; U.S. patent application Ser. No. 14/256,759, entitled "HAND-HELD MEDICAL IMAGING SYSTEM WITH THUMB CONTROLLER AND ASSOCIATED SYSTEMS AND METHODS" and U.S. patent application Ser. No. 14/301,299, entitled "SYSTEMS AND METHODS FOR COOLING ULTRASOUND TRANSDUCERS." The foregoing applications are incorporated by reference herein in their entireties.

TECHNICAL FIELD

Systems and methods of dissipating heat from a medical imaging device are disclosed herein.

DETAILED DESCRIPTION

The disclosed technology is generally directed to systems and methods of removing heat from a handheld medical imaging device (e.g., an ultrasound imaging device). In one embodiment, a handheld medical imaging device includes a housing having a number of a heat-producing electronic components (e.g., one or more processors, FPGAs and/or ASICs) used to process and display ultrasound data. The electronics are configured to receive signals from a medical imaging probe and process the signals to construct one or more medical images (e.g., one or more ultrasound images). The housing also includes a heat sink positioned near a perimeter of the housing at a location that is away from a handle where the user grasps the device. The heat sink is positioned adjacent to, and thermally coupled with, one or more heat producing components in the imaging device. One or more heat pipes are connected to the heat sink in order to direct heat produced from components that are located on the interior of the housing into the heat sink. In some embodiments, the heat sink is configured to dissipate heat into a slot formed between the housing and an outer edge of the imaging device. The slot is sized to prevent accessibility to the heat sink by a finger of an operator. In some aspects, the device weighs about 2 kg or less (e.g., between about 0.5 kg and about 1 kg (between about 1 pound or between about 2 pounds), or about 0.54 kg (1.2 pounds)), and the surface area of the housing including is less than about 500 square centimeters. The heat pipe and heat sink and software controls are configured to maintain a temperature of the housing at a predetermined temperature less than 48 degrees Celsius during image processing operations.

In certain aspects, a first thermal sensor is positioned at a first end portion of the housing, and a second thermal sensor is positioned between a second end portion and an intermediate portion of the housing. The first and second thermal sensors can be operatively coupled to the electronics, and can be configured to provide corresponding first and second signals indicative of temperature measurements acquired at the first and second thermal sensors. In some aspects, the electronics are configured to temporarily cease operations if the first and second signals indicate a difference in temperature greater than or equal to a predetermined temperatures (e.g., about 1 degree Celsius, about 2 degrees Celsius, about 3 degrees Celsius, about 5 degrees Celsius, between about 5 degrees Celsius and about 10 degrees Celsius).

It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with reference to FIGS. 1A-4B.

Figure 1A:
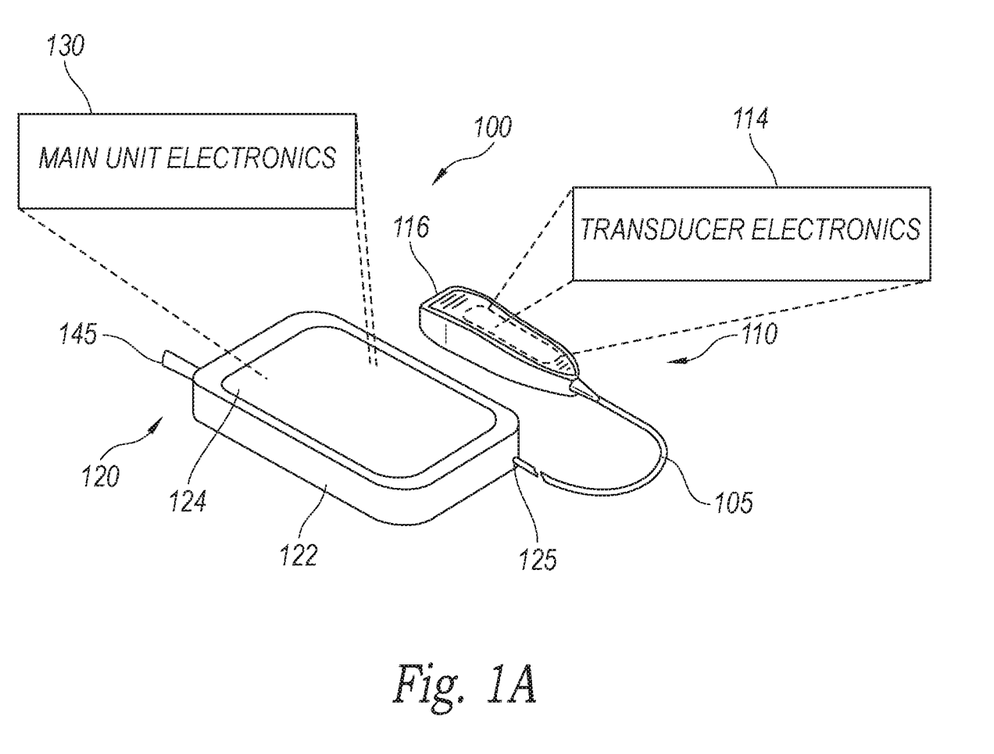
FIG. 1A is a schematic isometric view of a medical imaging system configured in accordance with an embodiment of the disclosed technology.

FIG. 1A is a schematic isometric view of a medical imaging system or a portable ultrasound system 100 ("system 100"). The system 100 includes a medical imaging probe, or an ultrasound transducer probe 110, coupled to a main unit 120 by a cable 105. The ultrasound transducer probe 110 includes an ultrasound transducer assembly 116 coupled to transducer electronics 114 inside the ultrasound transducer probe 110. As described in further detail below in reference to FIG. 1B, the transducer electronics 114 may include, for example, one or more beam formers, processors, analog-to-digital converters, etc. The ultrasound transducer probe 110 is configured to transmit ultrasound energy from the ultrasound transducer assembly 116, and receive ultrasound echoes at the ultrasound transducer assembly 116. The ultrasound transducer assembly 116 converts the received ultrasound echoes to electronic signals, which are transmitted to the main unit 120 via the cable 105. The main unit 120 includes a housing 122, in which a number of components including a display 124 (e.g., a touchscreen display), and an antenna or communications components 145 are located. An aperture 125 in the housing 122 receives a connector from the cable 105 to connect the main unit 120 to the transducer probe 110. Main unit electronics 130 in the housing 122 receive the signals from the ultrasound transducer probe 110 and process the signals to form one or more ultrasound images, which can be displayed to a user on the display 124.

Figure 1B:
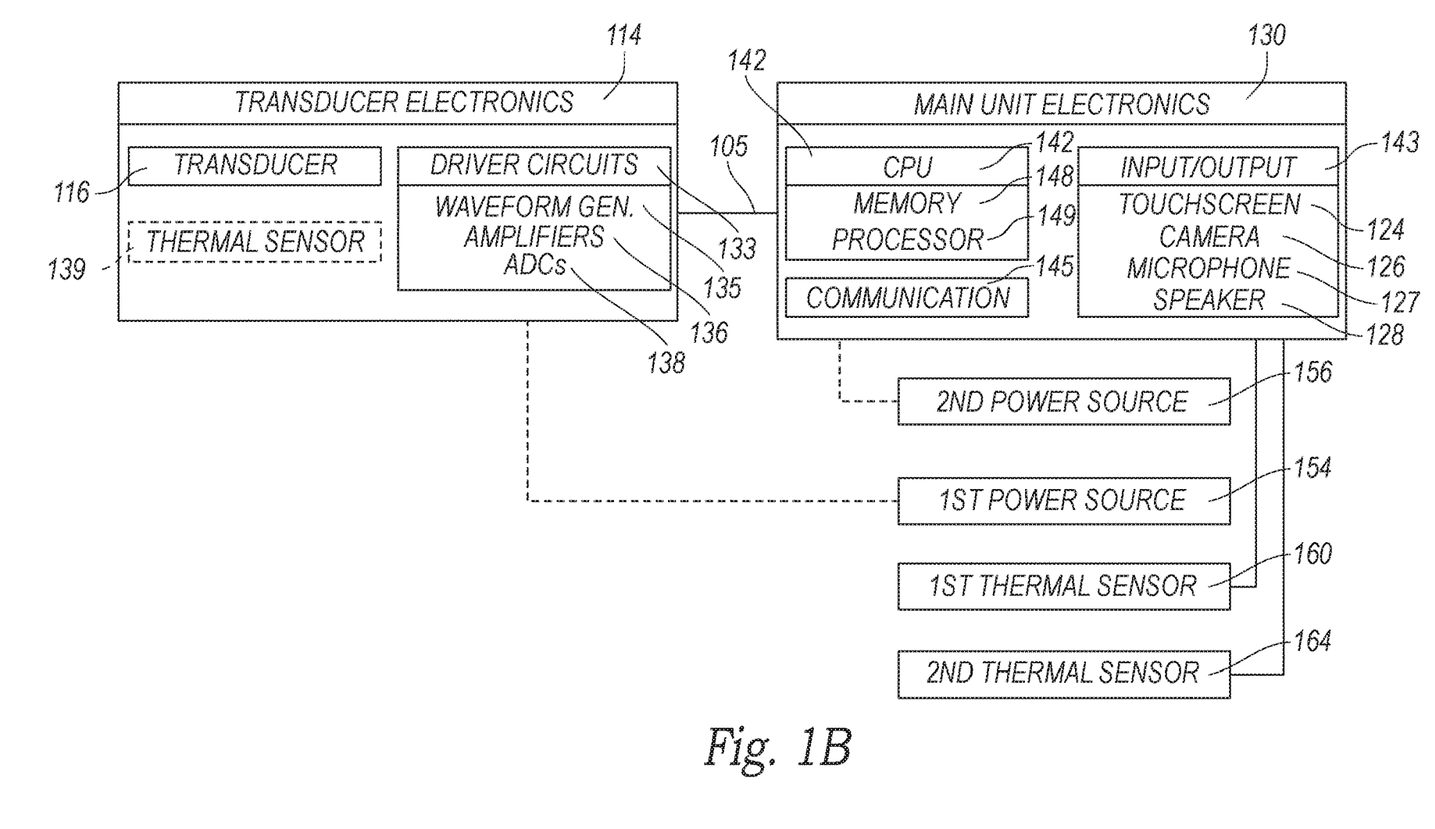
FIG. 1B is a functional block diagram of a medical imaging system configured in accordance with an embodiment of the disclosed technology.

FIG. 1B is a schematic block diagram of various electronic components of the system 100 configured in accordance with an embodiment of the disclosure. The system 100 includes the transducer electronics 114 in the ultrasound transducer probe 110 (FIG. 1A) and main unit electronics 130 at the main unit 120 (FIG. 1A). The transducer electronics 114 include one or more driver circuits 133 configured to operate the ultrasound transducer assembly 116. The driver circuits 133 can include, for example, waveform generators 135, amplifiers 136, analog to digital converters (ADCs) 138, and other ultrasound signal processing components (e.g., a CPU, controller, transmit/receive beam former circuitry, etc.). In some embodiments, at least a portion of the driver circuits 133 can be located in the main unit 120. Moreover, in some embodiments, a thermal sensor 139 is optionally coupled to the transducer electronics 114. The thermal sensor 139 can be configured to transmit signals indicative of a temperature within the ultrasound transducer probe 110 and/or an outer surface thereof to the main unit 120. If a temperature of the ultrasound transducer probe 110 exceeds a predetermined temperature (e.g., 40 degrees Celsius), the transducer electronics 114 may be configured to cease and/or reduce operations until the temperature received from the thermal sensor 139 falls below the predetermined temperature.

The main unit electronics 130 include a CPU 142, input/out devices 143, and the communications components 145. The CPU 142 includes a memory 148 and a programmable processor 149 configured to execute instructions that are stored in the memory 148 in order to perform various processes, logic flows, and routines. The input/out devices 143 can include, for example, the display 124, a camera 126, a microphone 127, and/or a speaker 128. The communications components 145 can include a network adaptor, a wireless transceiver (e.g., Wi-Fi or cellular transceiver), or other suitable components for communication over a wired or wireless communication network such as the Internet, local area network or the like.

In one embodiment, a first thermal sensor 160 is disposed at a first location in the housing 122 (FIG. 1A) near where a user holds the imaging system and a second thermal sensor 164 is disposed at a second location in the housing 122 at a point away from where the user holds the imaging system. The first and second thermal sensors 160 and 164 are configured to transmit first and second signals, respectively, indicative of temperature readings at the first and second locations. In some embodiments, if the first and second signals indicate a temperature gradient greater than a predetermined, maximum temperature gradient (e.g., a 1 degree Celsius gradient, a 3 degree Celsius gradient, a 5 degree Celsius gradient or the like), the main unit electronics 130 may be configured to cease and/or reduce processing operations and warn the user via an on-screen message that the unit has faulted. If either signal indicates a temperature greater than a predetermined maximum value the main unit electronics 130 may be configured to provide a warning message to the user that the device will shut down. If either signal indicates a temperature greater than a higher predetermined maximum value the main unit electronics 130 may be configured to shut down the device until the temperature lowers by natural cooling.

In some embodiments, the transducer electronics 114 are powered by a first dedicated power source device, or first battery 154, and the main unit electronics 130 are powered by a second dedicated power source device, or second battery 156. In the illustrated embodiment, both the first and second batteries 154 and 156 are located at the main unit 120. The first battery 154 can include, for example, a removable battery, and the second battery 156 can include, for example, an internal battery. In one embodiment, the internal battery can be integrally coupled to the main unit electronics 130. Additional information about power management systems and methods can be found, for example, in the Applicant's co-pending U.S. patent application Ser. No. 14/256,731, incorporated by reference above in its entirety.

In operation, the driver circuits 133 can operate the ultrasound transducer assembly 116 to produce and steer an acoustic signal toward a target region of interest. The main unit electronics 130, in turn, can drive the driver circuits 133 based on user input. For example, as described in greater detail below, the user can provide input by operating various graphical controls presented at the display 124.

As explained in more detail below with reference to FIGS. 2A through 4B, portable ultrasound devices can produce a significant amount of heat. Conventional ultrasound systems that have large surface areas and volumes can accommodate fans and/or other cooling systems to dissipate the heat that is produced by electronics during image processing. In a small housing, such as the housing 122 of the main unit 120, there is no room to accommodate large active cooling systems in addition to the components required to produce high quality ultrasound images. Embodiments of the disclosed technology therefore include a heat sink positioned near a perimeter of the housing that passively dissipates heat from the housing. Heat producing components are thermally coupled to and are physically located near the heat sink. In addition, the housing includes one or more heat pipes that are configured to direct heat into the heat sink that is received from heat producing components that are located at positions away from the heat sink. Moreover, embodiments of the disclosed technology remove heat from the device without producing vibration, thereby potentially reducing stress on the operator's wrist as he or she holds the main unit 120.

Figure 2A:
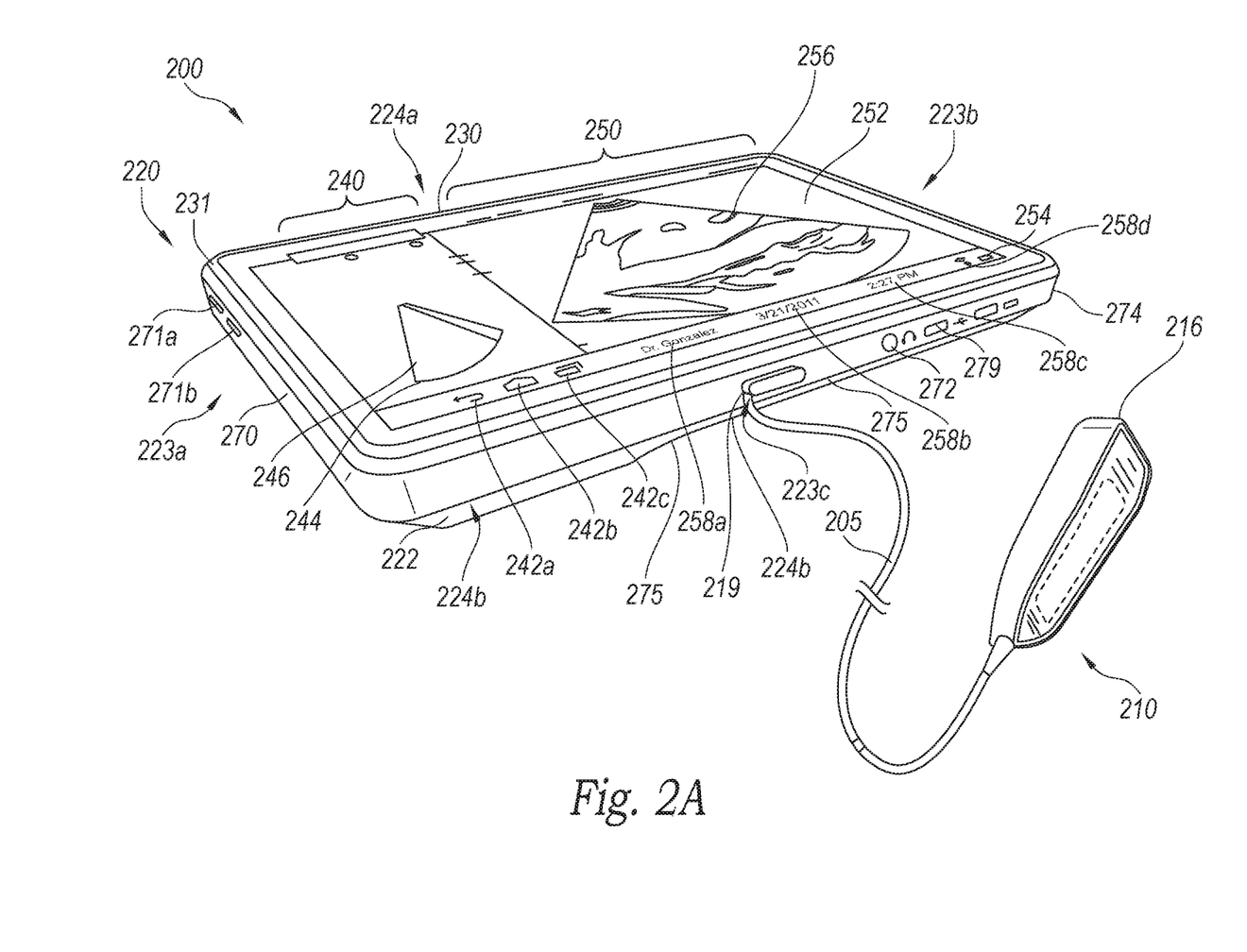
FIG. 2A is an isometric top view of a medical imaging device configured in accordance with an embodiment of the disclosed technology.
Figure 2B:
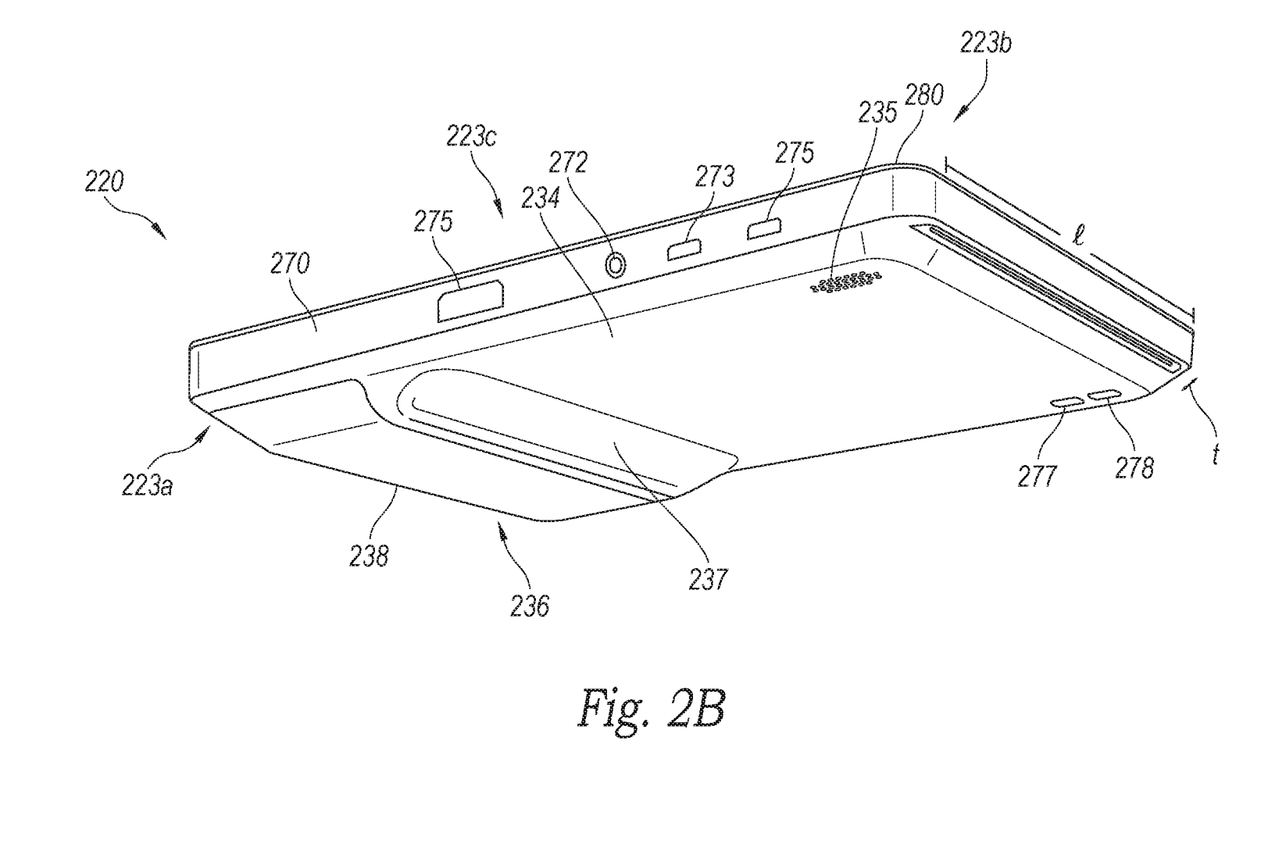
FIG. 2B is an isometric underside view of a portion of the medical imaging device of FIG. 2A.

FIG. 2A is an isometric top view of an ultrasound system 200 configured in accordance with embodiments of the disclosed technology. FIG. 2B is an isometric underside view of the ultrasound system 200. Referring to FIGS. 2A and 2B together, the ultrasound system 200 includes an ultrasound probe 210 that is removably coupled to a display unit or main unit 220 by a cable 205. The ultrasound probe 210 (e.g., the ultrasound transducer probe 110 of FIG. 1A) includes an ultrasound transducer 216 configured to transmit ultrasound energy and receive ultrasound echoes from a patient's tissue. Signals corresponding to the received ultrasound energy are converted into digital form and transmitted to the main unit 220 via the cable 205.

The main unit 220 includes an enclosure or a housing 222. The housing 222 has a first end portion 223a opposite a second end portion 223b with a middle or intermediate portion 223c therebetween. In some embodiments, for example, the housing 222 can have a surface area between about 250 square centimeters and about 1000 square centimeters, or approximately 500 square centimeters (e.g., 20 cm×10 cm×2.5 cm). In other embodiments, however, the housing 222 can have any suitable dimensions and surface area. In some embodiments, the housing is made of plastic.

A receptacle 275 on the outer edge of the housing is configured to receive a connector 219 on one end of the cable 205. A display 230 carried by the housing 222 is surrounded by a bezel 231 curved outward from the display 230 toward an exoskeletal member or a band 270 surrounding the perimeter of the housing 222. In some embodiment, the band 270 comprises a material (e.g., a metal) and the housing 222 comprises a different material (e.g., a plastic). Controls 271a and 271b in the band 270 can be configured to have a number of functions including selection functions, user input functions, volume up and down control functions, etc. A port 272 on an edge of the housing 222 is configured to receive a headphone jack. An interface receptacle 273 is configured to receive a data cable connector (e.g., a USB cable connector, a Thunderbolt data connector and/or another suitable data interface). An interface receptacle 274 is configured to receive a video cable connector (e.g., an HDMI connector, a DisplayPort connector, a DVI connector and/or another suitable video interface).

The display 230 includes a first display area 240, and a second display area 250. The first display area 240 includes a plurality of controls 242a (e.g., a back button), 242b (e.g., a home button) and 242c (e.g., an application switcher button). A user input area 244 is configured to receive touch input in one or more input fields 246 from the one or more of digits (e.g., a thumb) on the operator's hand. Additional information about the systems and methods of displaying information and/or receiving input can be found, for example, in the applicant's co-pending U.S. patent application Ser. Nos. 14/256,744 and 14/256,759, incorporated by reference above in their entireties. The second display area 250 shown in the display 230 includes an upper portion 252 and a lower portion 254. The upper portion 252 is configured to display one or more ultrasound images 256. The lower portion 254 is configured to display various pieces of information about the measurement including measurement information 258a (e.g., an operator's name), 258b (e.g., a measurement date), 258c (a measurement time) and 258d (e.g., a wifi status indicator).

Referring now only to FIG. 2B, a battery pocket 236 (not visible) in the underside surface 234 of the housing 222 receives a battery 238. A groove 237, formed in the underside surface 234 of the housing 222, is configured to conform to a portion of an operator's hand. In some embodiments, for example, the groove 237 is shaped to receive one or more digits and/or fingertips of an operator's hand (e.g., a left hand), while the operator holds the device and can at least partially control the device with a thumb (e.g., a left thumb) on the display 230. Translucent panels 277 and 278 on the housing surface allow light to pass through to a camera and flash (not shown), respectively, that are positioned inside the housing 222.

In one embodiment the housing includes a vent, an aperture or a slot 280 positioned on a side away from where the user holds the housing. The slot 280 is dimensioned so that a user's finger cannot touch a heat sink that is positioned behind the slot 280. In some instances, for example, the temperature of the heat sink can exceed a maximum temperature that is higher than is acceptable for a medical device. The slot 280 allows air to reach the heat sink in order to dissipate heat from the heat sink and out of the housing 222 without allowing the heat sink to be touched by an operator's fingers.

Figure 3A:
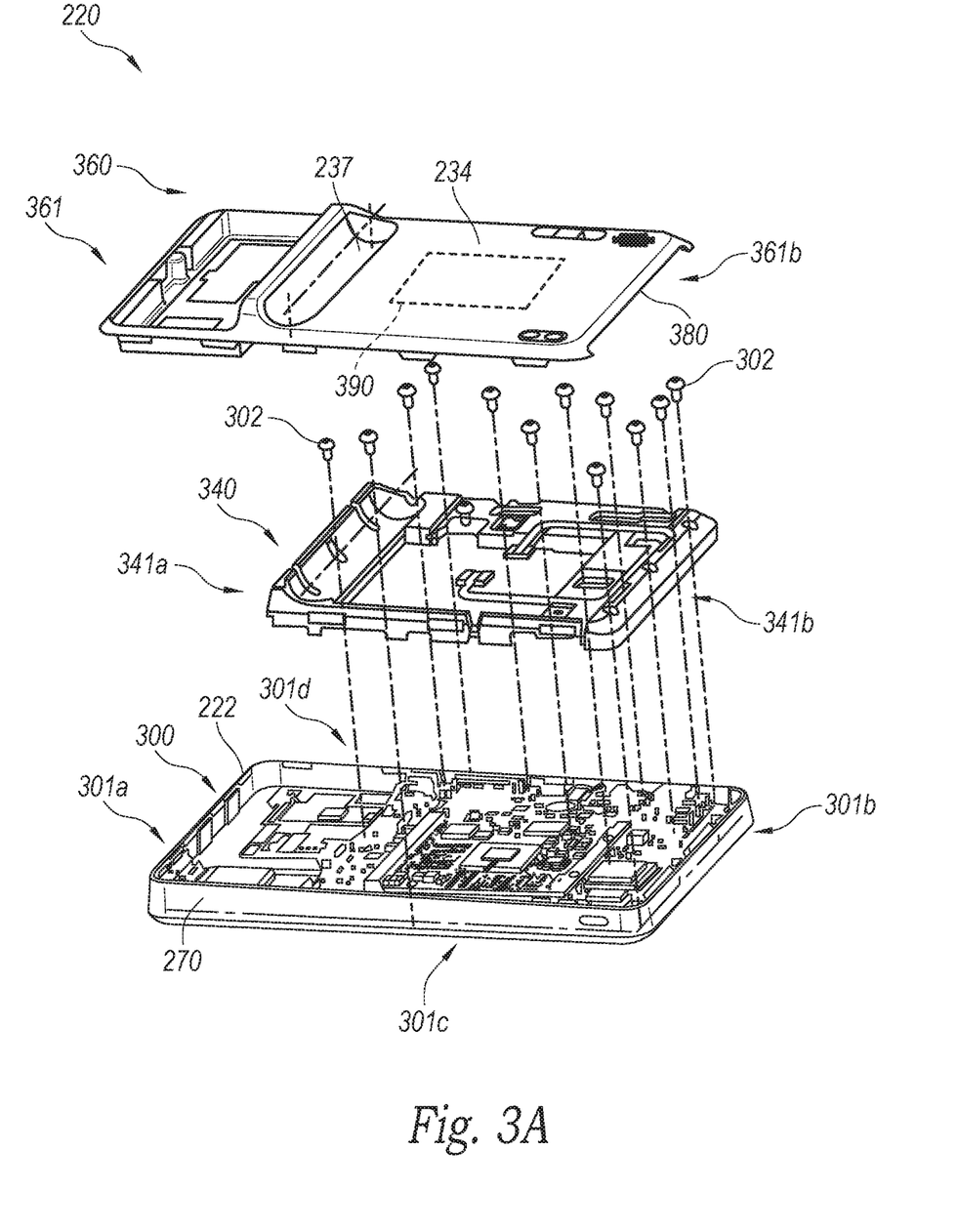
FIG. 3A is an exploded view of the medical imaging device of FIGS. 2A and 2B configured in accordance with an embodiment of the disclosed technology.

FIG. 3A is an exploded view of the main unit 220 of the ultrasound system 200 shown in FIGS. 2A and 2B. The main unit 220 includes a base portion 300, a frame 340, and a cover 360. In one embodiment, the frame 340 comprises a plastic (e.g., polycarbonate, ABS). In some embodiments, the band 270 is integrally formed with the frame 340. The base portion 300 is attached to the frame 340 via a plurality of fasteners 302 (e.g. screws). The lower cover is removably attachable to the base portion 300. In embodiment, for example, the cover 360 snaps and unsnaps onto the base portion 300. A heat spreader 390 imbedded in the cover 360, or attached to underside portion thereof, is configured to spread heat produced by electronics in the main unit 220 to reduce thermal gradients through the housing 222 during operation. In some embodiments, the heat spreader 390 comprises graphite. In other embodiments, however, the heat spreader comprises another suitable thermally conductive material (e.g., copper).

Figure 3B:
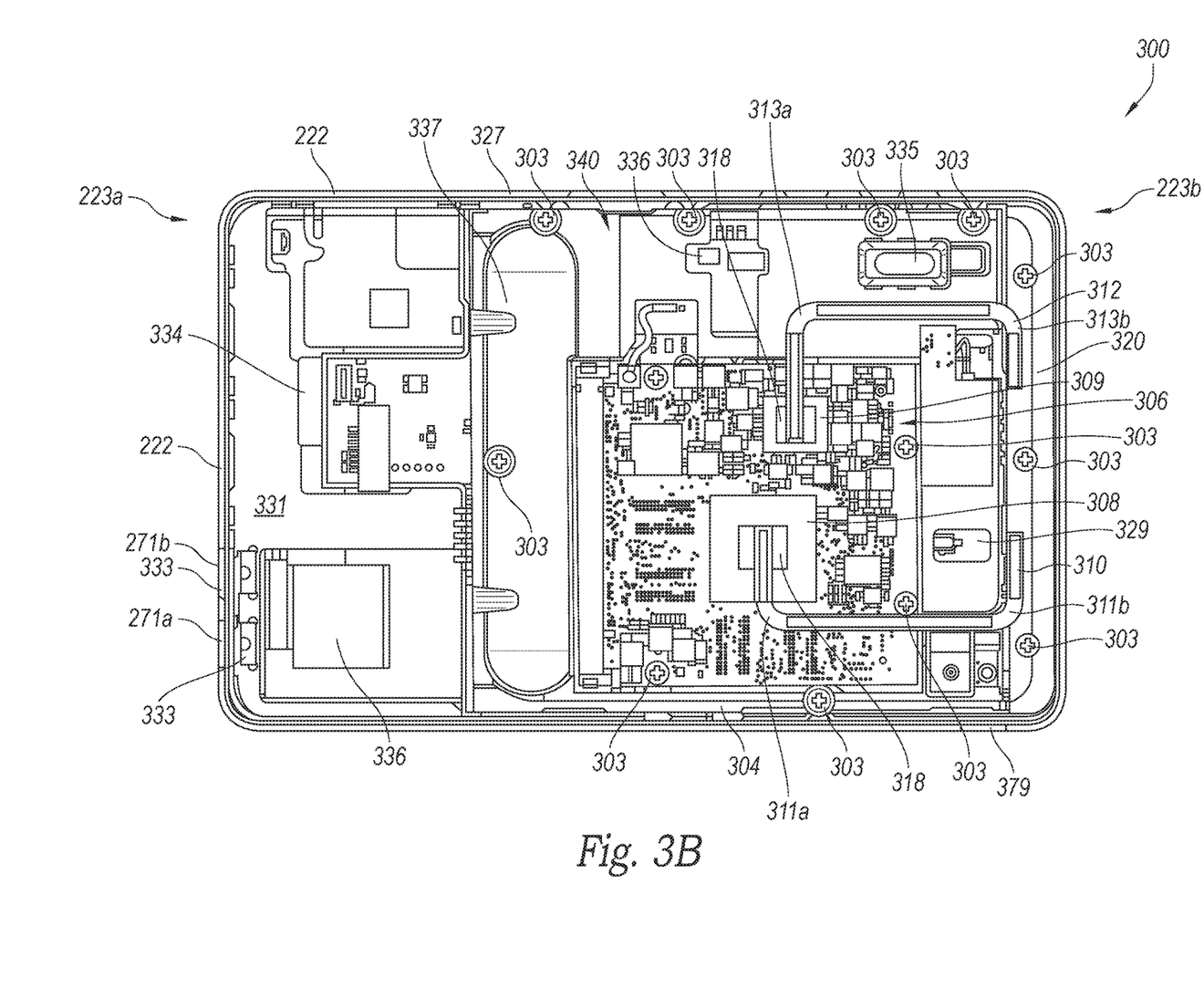
FIG. 3B illustrates a layout of components in a bottom portion of a medical imaging device in accordance with an embodiment of the disclosed technology.
Figure 3C:
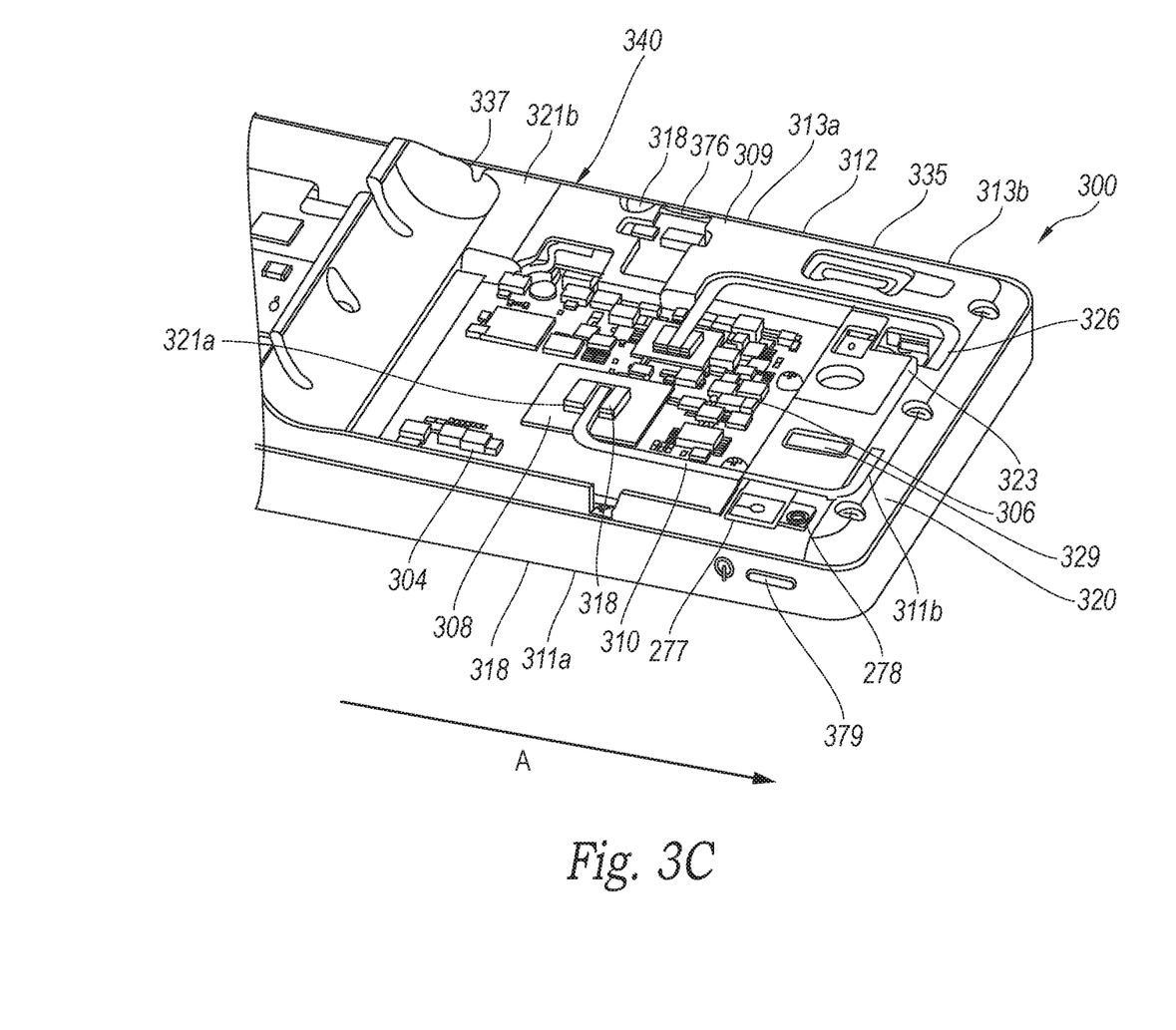
FIG. 3C illustrates a cooling mechanism for a medical imaging device in accordance with an embodiment of the disclosed technology.
Figure 3D:
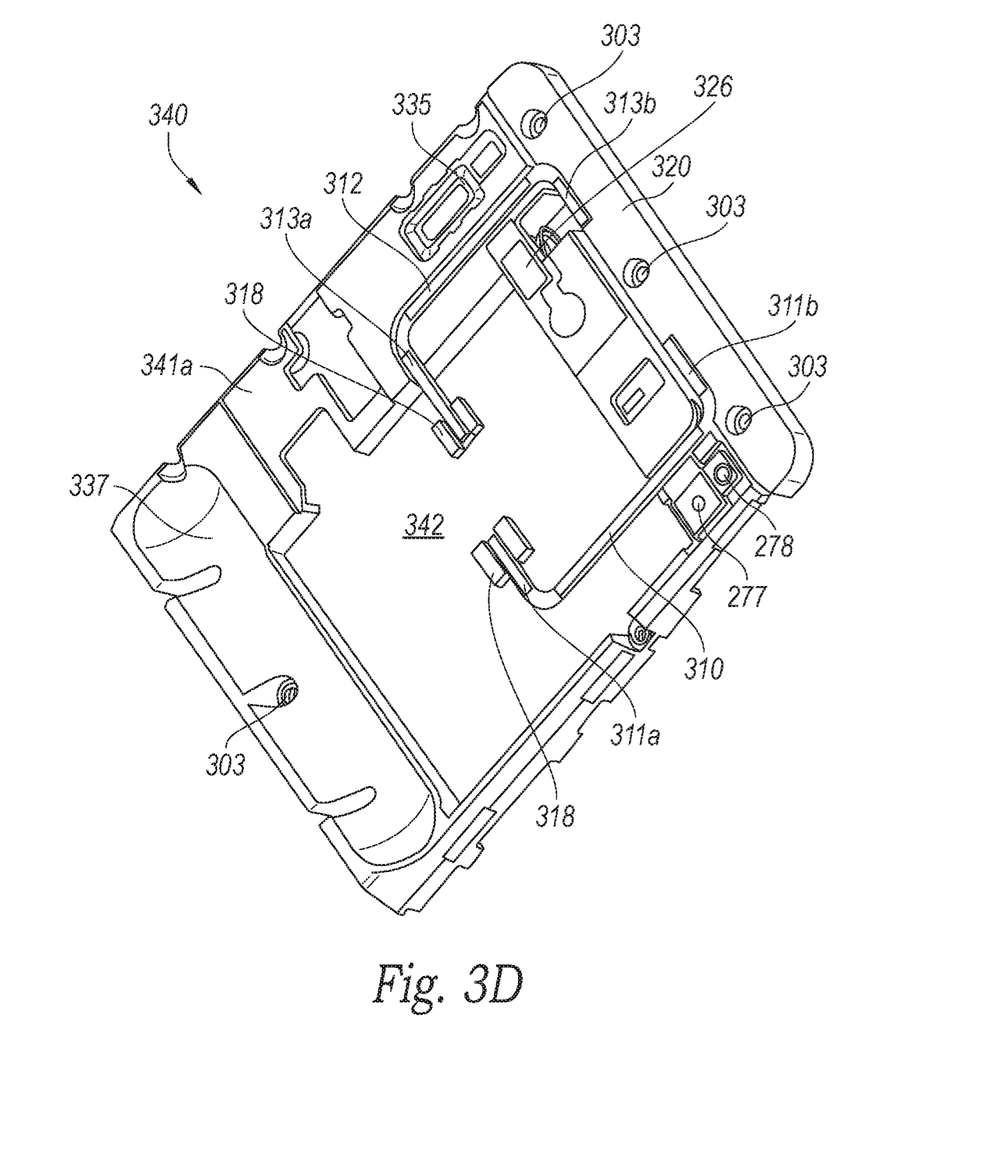
FIGS. 3D and 3E illustrate a number of heat pipes within a medical imaging device in accordance with an embodiment of the disclosed technology.
Figure 3E:
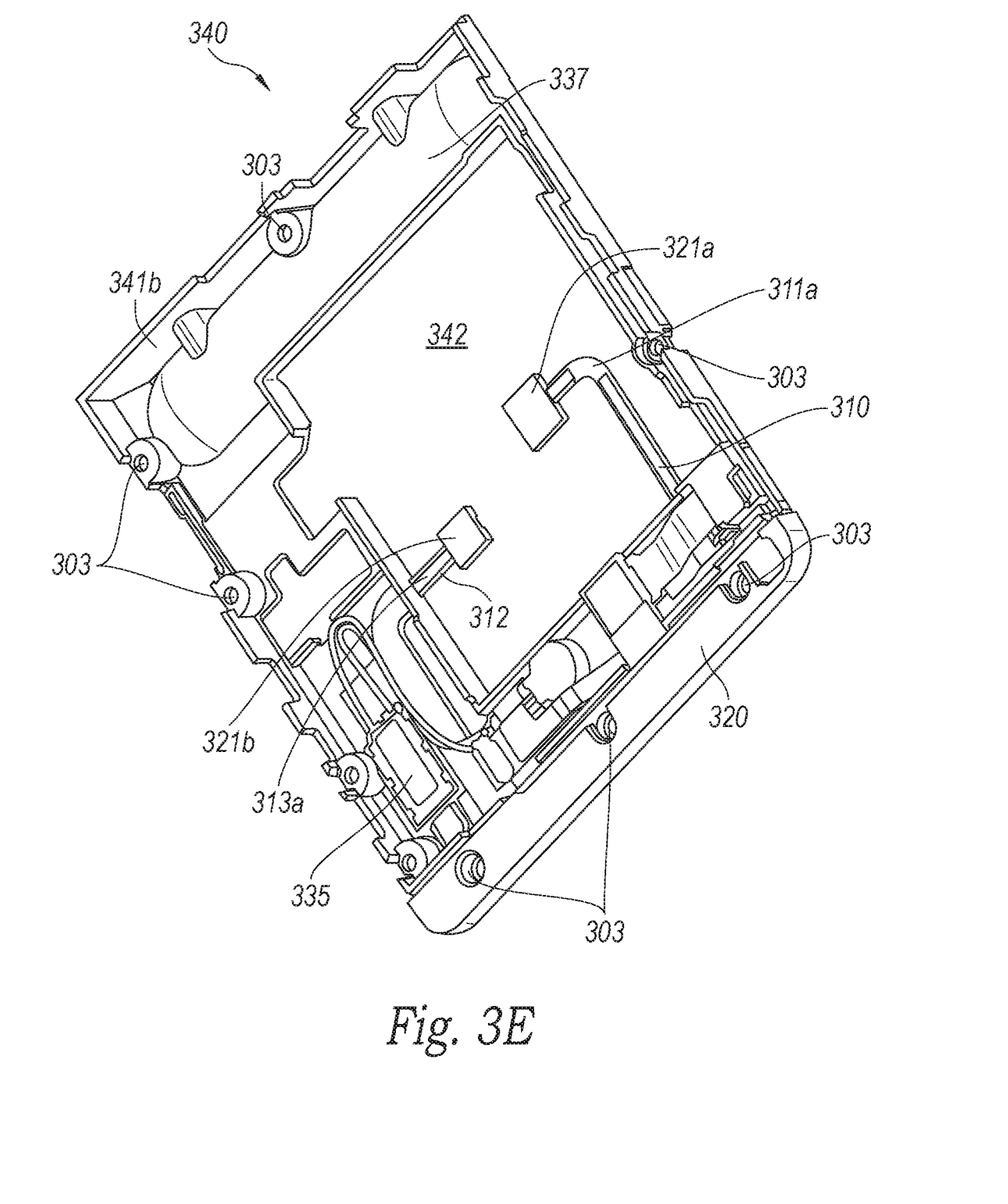
Figure 4A:
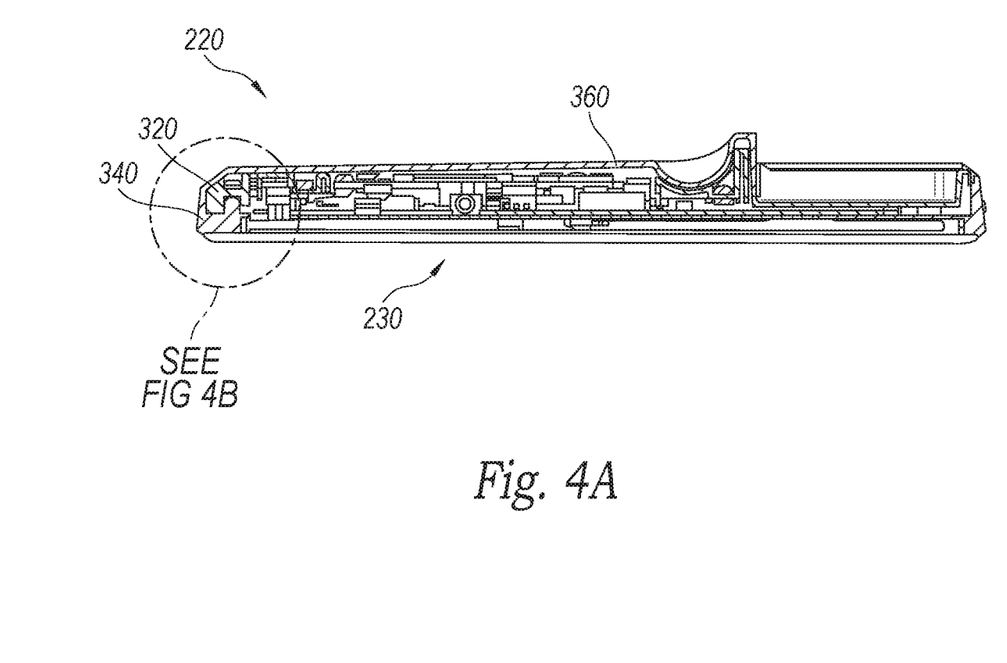
FIG. 4A is a side section view of a medical imaging device in accordance with an embodiment of the disclosed technology.
Figure 4B:
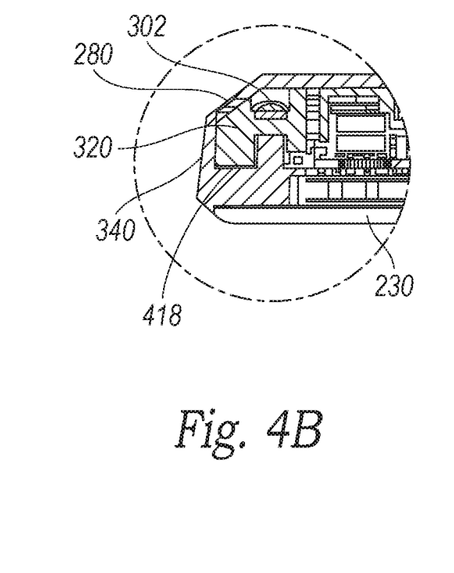
FIG. 4B is an enlarged view of a portion of FIG. 4A.

FIG. 3B is a top view of the base portion 300. FIG. 3C is a side isometric view of the base portion 300. FIGS. 3D and 3E are isometric views of a lower surface and an upper surface, respectively, of the frame 340. FIG. 4A is a side section view of the main unit 220. FIG. 4B is an enlarged view of a portion of FIG. 4A. Referring first to FIGS. 3B, 3D and 3E, a void 342 in the frame 340 is configured to receive system electronics 306 when the frame 340 is attached to the base portion 300. A recess 331 is configured to receive a battery for power. A speaker 335 is configured to output audio information. A Wi-Fi antenna 336 is configured to couple the device to a communications network. A groove 337 in the frame 340 corresponds to the groove 237 formed in the underside surface 234 of the cover 360. A haptic motor 323 (FIG. 3C) at the second end portion 223b produces minute movements in response to touch input by the operator. A display FPGA 329 (FIG. 3B) is configured to control the display of pixels on the display 230 (FIGS. 2A and 2B).

As those of ordinary skill will appreciate, the system electronics 306 can produce significant amounts of heat during image processing operations. Without a means of removing heat, the heat emitted by the system electronics 306 can cause the temperatures of one or more surfaces of the housing 222 (FIGS. 2A and 2B) to exceed a predetermined temperature (e.g., 48 degrees C.) that could render the housing 222 too hot for an operator to hold. Conventional ultrasound devices may have housings or cabinets sufficiently large to include one or more cooling systems or devices (e.g., one or more fans and/or other active cooling systems) configured to reduce heat levels. As devices shrink in size, however, there is space and/or weight requirements may not allow the use active cooling devices. Moreover, there may be a desire or preference to operate a medical imaging device in the absence of a fan or another cooling device that can produce sound and/or require periodic cleaning due to, for example, an accumulation of dust. Embodiments of the disclosed technology are configured to dissipate thermal energy in housing 222 emitted from the system electronics 306 and/or other and/or other components of the main unit 220 (e.g., the display 230 of FIG. 2A), toward the heat sink 320 and away from the operator's hand at the first end portion 223a (FIG. 2A) of the housing 222. Embodiments of the disclosed technology are also configured to reduce temperature gradients in the housing 222 thereby reducing thermal expansion in the housing 222.

Referring now to FIGS. 3B, 3C, 4A and 4B, the base portion 300 includes the system electronics 306 (e.g., the main unit electronics 140 of FIGS. 1A and 1B) mounted on a substrate 304. As discussed above, the imaging system includes a heat sink 320 that is positioned adjacent an interior portion of the slot 280 on an edge of the device away from where user holds the device. The heat sink 320 comprises a thermally conductive material (e.g., aluminum) is configured to receive and dissipate heat from one or more of the components in the unit that generate the most heat when operating. In the illustrated embodiment of FIGS. 3B and 3C, for example, the heat sink 320 comprises an outer edge of the frame 340 such that the heat sink 320 has a shape that conforms to interior surface of the cover 360 and/or another surface of the housing 222 (FIGS. 2A and 2B). The shape of the heat sink 320 conforming to an edge of the cover 360 allows placement immediately behind and/or adjacent the slot 280 (FIG. 2B) to increase an amount of air transferred from the heat sink 320 to outside air via the slot 280. In certain device orientations, An increase in the amount of air transferred near the heat sink 320 generally leads to a greater amount of heat that can be exhausted from the heat sink 320 via the slot 280. In some embodiments, the heat sink 320 is mechanically coupled to the frame 340 while at least partially thermally shielded from the frame 340. In one embodiment, for example, the heat sink 320 is attached to the frame 340 with a thermally insulative material 418 (FIG. 4B) (e.g., urethane foam, polyester plastic) therebetween to reduce an amount of heat conducted from the heat sink 320 to the frame 340. Thermally insulating or decoupling the heat sink 320 from the frame 340 can prevent recirculation of heat into the main unit 220 from heat at the heat sink 320 received from components in the main unit 220 via the heat pipes 310 and 312. In some embodiments, the heat sink 320 comprises one or more fins or finned surfaces.

Embodiments of the present disclosure are configured to direct heat from heat producing components toward the heat sink 320 and the slot 280 (FIG. 2B) away from the hand of the operator as he or she grips the main unit 220 along the groove 237. Embodiments of the present disclosure are further configured reduce an amount of heat that is transferred into the frame 340, thereby reducing surface temperatures of the housing 222 without the use of an active cooling system and/or a fan.

Referring now to FIGS. 3B, 3C and 3D, in one embodiment, a component such as, for example, the display FPGA 329 is positioned in thermal contact with the heat sink 320 to further facilitate heat dissipation therefrom. In some embodiments, a heat shunt (e.g., a copper member or bar)(not shown) is sandwiched between the display FPGA 329 and the heat sink 320 to facilitate heat transfer from the display FPGA 329 to the heat sink 320. The system electronics 306 include heat producing components including a first heat-producing component 308 (e.g. a processor) and a second heat-producing component 309 (e.g., an power management integrated circuit). The system electronics can further include other components such as, a one or more additional processors, converters, ASICs, FPGAs, and/or beam formers, and/or other electronic components used in the generation of ultrasound and/or in image processing of ultrasound signals to produce ultrasound images.

Because not all the components can be located in thermal contact with the heat sink 320, the imaging system includes a heat shunt, a, heat dissipation member or a first heat pipe 310 in thermal communication with a first heat conduction pad 321a (FIGS. 3C and 3E) on the first heat-producing component 308. The first heat pipe 310 includes an evaporator portion or a first end portion 311a, and a condensing portion or a second end portion 311b that is thermally coupled to the heat sink 320. A heat shunt, heat dissipation member or a second heat pipe 312 is in thermal communication with a second heat conduction pad 321b (FIGS. 3C and 3E) on a second heat-producing component 309 and includes an evaporator portion or a first end portion 313a and a condenser portion or a second end portion 313b that is thermally coupled to the heat sink 320. Components in the main unit 220 that generate significant amounts of heat are thermally coupled to the first and second heat conduction pads 321a and 321b to direct heat through the heat pipes 310 and 312 and into the heat sink 320. In some embodiments, cavities (not shown) extend through interior portions of the first heat pipe 310 and the second heat pipe 312 is configured to carry a working fluid (e.g., water, alcohol) therethrough. In some embodiments, the first heat pipe 310 and the second heat pipe 312 comprise copper. In other embodiments, however, the first heat pipe 310 and the second heat pipe 312 include any suitable thermally conductive material. In certain embodiments, the first heat pipe 310 and the second heat pipe 312 comprise one or more heat pipes manufactured by Fujikura Ltd. of Japan.

A pair of a plurality of thermal insulators 318 (e.g., pads comprising urethane foam or another suitable thermally insulative material) thermally insulate the first end portion 311a of the first heat pipe 310 from the cover 360. Another pair of the plurality of thermal insulators 318 thermally insulate the first end portion 313a of the second heat pipe 312 from the cover 360. The thermal insulators 318 can prevent contact between the heat pipes 310 and 312, which can reduce an amount of heat that is thermally conducted and/or radiated from the heat pipes 310 and 312 into the cover 360. Transferring heat produced by the system electronics via the heat pipes 310 and 312 toward the heat sink 320 reduces an amount of heat that reaches the cover 360 thereby allowing the system electronics 306 to perform more operations while causing lower temperatures at the cover 360 than in a device without the heat pipes 310 and 312 transferring heat to the heat sink 320. Transferring heat produced by the system electronics 306 to the heat sink 320 also allows for lower junction temperatures in the first heat-producing component 308 and second heat-producing component 309 allowing for improved performance across a larger range of environmental temperatures.

The base portion 300 further includes a first thermal sensor 326 and a second thermal sensor 327 coupled to the system electronics 306. The first thermal sensor 326 positioned at a first location in the housing 222 at the base portion 300. The second thermal sensor 327 is positioned at a second location in the housing 222 at the main unit 220. The first thermal sensor 326 and the second thermal sensor 327 are configured to produce first and second signals, respectively, corresponding to temperatures at the first and second locations. The system electronics 306 may be configured to receive the first and second signals from the first and second sensors, respectively. In some embodiment, the system electronics 306 are configured to cease operating and/or reduce processing operations if the first and second signals indicate a temperature gradient between the first and second locations in the housing 222 and/or the base portion 300 greater than a predetermined temperature gradient (e.g., between about 1 degree Celsius and about 10 degrees Celsius, or about 5 degrees Celsius).

In some embodiments, one or more of the components of the base portion 300 can include thermal sensors. For example, the first heat-producing component 308 and display FPGA 329 may each have built in thermal sensors (not shown) and configured to transmit first, second, and third signals, respectively, indicative of temperature readings within the respective components. In some embodiments, if these signals indicate a temperature gradient greater than a predetermined, maximum temperature gradient (e.g., a 1 degree Celsius gradient, a 3 degree Celsius gradient, a 5 degree Celsius gradient or the like), the main unit electronics 130 may be configured to cease processing operations and warn the user via an on-screen message that the unit has faulted. If any signal indicates a temperature greater than a predetermined maximum value the main unit electronics 130 may be configured to provide a warning message to the user that the device will shut down. If either signal indicates a temperature greater than a higher predetermined maximum value the main unit electronics 130 may be configured to shut down the device until the temperature lowers by natural cooling.

In operation, the first and second heat pipes 310 and 312 conduct or otherwise transmit heat from the system electronics 306 toward the heat sink 320 in the direction of an arrow A (FIG. 3C). The working fluid in the first and second heat pipes 310 and 312 can convert from a liquid to a vapor in the presence of sufficient heat (e.g., heat emitted during image processing operations) at a first temperature. The conversion of the working fluid in the first heat pipe 310 from a liquid to a vapor absorbs heat at the first end portion 311a. The working fluid vapor travels through the cavity (not shown) in the first heat pipe 310 from the first end portion 311a toward the second end portion 311b. The second end portion 311b can have a second, lower temperature than the first temperature of the first end portion 311a due to a proximity of the second end portion 311b to the heat sink 320 and the slot 280 (FIG. 2B). Accordingly, the working fluid at the second end portion 311b condenses to a liquid. The condensation of the working fluid from a vapor to a liquid removes heat from the second end portion 311b to the heat sink 320. The heat sink 320 discharges the heat out of the main unit 220 via the slot 280 (FIG. 2B) thereby reducing a temperature level within the main unit 220 and the housing 222.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. An ultrasound imaging system, comprising:
a first housing having a first side; a second side that is opposite to the first side; a distal end portion; and a proximal end portion that is opposite to the distal end portion; a display on the second side between the distal end portion and the proximal end portion, wherein the proximal end portion includes a handle that is configured to receive at least a portion of an operator's hand for an operator to hold the first housing, wherein the first side is between the proximal end portion and the distal end portion;
a second housing coupled to the first housing configured to carry a transducer assembly;
electronics in the first housing coupled to the display, the electronics configured to:
  receive electronic signals from the transducer assembly,
  generate one or more ultrasound images based on the electronic signals; and
  output the one or more ultrasound images to the display, wherein
the first housing includes a frame between the first side and the second side, the frame including a first portion extending between the distal end portion and the proximal end portion along a first part of a perimeter of the first housing and a second portion extending between the distal end portion and the proximal end portion along a second part of the perimeter of the first housing that is opposite to the first portion and a third portion extending between the first portion and the second portion along a third part of the perimeter of the first housing, wherein the distal end portion includes a vent on the first side of the first housing; and
a heat sink disposed in the third portion of the frame adjacent to the vent at the distal end portion, the heat sink forming the third portion of the frame that is between the vent on the first side and the display on the second side of the first housing to passively dissipate heat from the display through the vent in the distal end portion to an outer edge of the first housing and away from the handle in the proximal end portion, wherein the heat sink is attached to the frame via a thermally insulating pad to form the portion of the frame and reduce the heat conducted from the heat sink to the frame; and
one or more heat transfer pipes comprising a first heat transfer pipe configured to transmit heat from the electronics toward the heat sink and away from the first side of the first housing, wherein at least a portion of the first heat transfer pipe is thermally insulated from the first housing by a pair of a plurality of thermal insulators to reduce an amount of heat that reaches the first housing;
a first temperature sensor at a first location that is at the handle in the proximate end portion of the first housing; and
a second temperature sensor at a second location in the first housing that is at the heat sink in the distal end portion of the first housing, wherein the first temperature sensor and the second temperature sensor are configured to produce a first signal indicating a first temperature at the handle and a second signal indicating a second temperature at the heat sink,
wherein the electronics are configured to receive the first signal and the second signal and to cease operating if a difference between the first temperature and the second temperature is greater than a threshold temperature.

2. The ultrasound imaging system of claim 1, wherein the first housing weighs less than 2 kg.

3. The ultrasound imaging system of claim 2, wherein surface area of the first housing is less than 500 square centimeters, and wherein the heat sink and the one or more heat transfer pipes are configured to maintain a temperature of the first side of the first housing to less than 48 degrees Celsius.

4. The ultrasound imaging system of claim 1, wherein the threshold temperature is less than or equal to 5 degrees Celsius.

5. The ultrasound imaging system of claim 1, wherein the first location in the first housing is closer to the first side of the first housing than to the heat sink.

6. The ultrasound imaging system of claim 1, wherein at least one of the one or more heat transfer pipes includes a cavity.

7. The ultrasound imaging system of claim 1, wherein the thermally insulating pad is positioned between the heat sink and the frame.

8. The ultrasound imaging system of claim 1, wherein the electronics comprise a first heat-producing component and a second heat-producing component that are disposed between the handle and the heat sink, and wherein the first heat transfer pipe extends from the first heat-producing component to the heat sink, and wherein the one or more heat transfer pipes include a second heat transfer pipe that extends from the second heat-producing component to the heat sink.

9. An ultrasound system, comprising:
a transducer assembly configured to generate ultrasound signals and electronic signals based on the ultrasound signals;
a housing having a first side; and a second side that is opposite to the first side; a distal end portion; and a proximal end portion that is opposite to the distal end portion, wherein the proximal end portion includes a handle that is configured to receive at least a portion of an operator's hand for an operator to hold the housing, wherein the first side is between the proximal end portion and the distal end portion, wherein the housing includes a frame between the first side and the second side, the frame including a first portion extending between the distal end portion and the proximal end portion along a first part of a perimeter of the first housing and a second portion extending between the distal end portion and the proximal end portion along a second part of the perimeter of the first housing that is opposite to the first portion and a third portion extending between the first portion and the second portion along a third part of the perimeter of the housing;
electronics on the second side in the housing configured to generate one or more ultrasound images based on the electronic signals and produce heat,
the distal end portion including a vent on the first side of the housing, and
a heat sink is in the third portion of the frame adjacent to the vent, wherein the heat sink forms the third portion of the frame that is between the vent on the first side and the electronics on the second side of the first housing to passively dissipate the heat from the electronics through the vent in the distal end portion to an outer edge of the housing and away from the handle in the proximal end portion, wherein the heat sink is attached to the frame via a thermally insulating pad to form the portion of the frame; and
one or more heat transfer pipes comprising a first heat transfer pipe configured to transmit the heat from the electronics toward the heat sink and away from the first side of the housing via the vent, wherein at least a portion of the first heat transfer pipe is thermally insulated from the first housing by a pair of a plurality of thermal insulators to reduce an amount of heat that reaches the first housing;
a first temperature sensor at a first location that is at the handle in the proximate end of portion of the first housing; and
a second temperature sensor at a second location in the housing that is at the heat sink in the distal end portion of the first housing, wherein the first temperature sensor is configured to produce a first signal indicating a first temperature at the handle and the second temperature sensor is configured to produce a second signal indicating a second temperature at the heat sink,
wherein the electronics are configured to reduce or cease processing operations if one or more of the first temperature and the second temperature is greater than a first threshold temperature, or if a difference between the first temperature and the second temperature is greater than a second threshold temperature.

10. The ultrasound system of claim 9, wherein the first threshold temperature is less than 48 degrees Celsius and wherein the second threshold temperature is less than or equal to 5 degrees Celsius.

11. The ultrasound system of claim 9, wherein the housing weighs less than 2 kg.

12. The ultrasound system of claim 9, wherein surface area of the housing is less than 500 square centimeters.

13. The ultrasound system of claim 9, wherein the first location in the first housing is closer to the first side of the housing than to the heat sink.

14. The ultrasound system of claim 9, wherein at least one of the one or more heat transfer pipes includes a cavity.

15. The ultrasound system of claim 9, wherein the electronics comprise a first heat-producing component and a second heat-producing component that are disposed between the handle and the heat sink.

16. The ultrasound system of claim 14, wherein the first heat transfer pipe extends from the first heat-producing component to the heat sink, and wherein the one or more heat transfer pipes include a second heat transfer pipe that extends from the second heat-producing component to the heat sink.

17. The ultrasound system of claim 9, further comprising:
a heat spreader at least partially embedded in the first side of the housing.

* * * * *